(12) United States Patent
Hsu

(10) Patent No.: US 7,156,107 B2
(45) Date of Patent: Jan. 2, 2007

(54) TEETH CLEANING BRUSH STRUCTURE

(75) Inventor: Walter Hsu, Yinlin Hsien (TW)

(73) Assignee: Welter's Co., Ltd., Yinlin Hsien (TW)

( * ) Notice: Subject to any disclaimer, the term of this patent is extended or adjusted under 35 U.S.C. 154(b) by 443 days.

(21) Appl. No.: 10/462,626

(22) Filed: Jun. 17, 2003

(65) Prior Publication Data
US 2004/0255970 A1 Dec. 23, 2004

(51) Int. Cl.
A45D 44/18 (2006.01)

(52) U.S. Cl. ...................... 132/309; 132/310

(58) Field of Classification Search ........ 132/308–311, 132/321, 328; 15/176.1, 206; 433/147; 16/430
See application file for complete search history.

(56) References Cited

U.S. PATENT DOCUMENTS 4,033,007 A * 7/1977 Hadary ........................ 15/172
4,780,923 A * 11/1988 Schultheiss ................... 15/111
4,919,156 A * 4/1990 Gipson ......................... 132/309
5,293,661 A * 3/1994 Appleby ...................... 15/167.1
6,247,477 B1 * 6/2001 Wagner ....................... 132/309

* cited by examiner

Primary Examiner—John J. Wilson
Assistant Examiner—Robyn Doan
(74) Attorney, Agent, or Firm—Troxell Law Office, PLLC

(57) ABSTRACT

A teeth cleaning brush structure including a cleaning brush, a cover, a stick sleeve, a cleaning rod, and a control device. The cleaning brush has bristles and a flexible insert rod extending from an end of the bristles. The cover has an open receiving groove located at one end forth stick sleeve with a cleaning stick disposed at one end to be inserted. The cleaning is equipped with a hollow retaining chamber located at a first end and coupling section extending from a second end matching a pivot section of the control device. The control device is mounted to the coupling section of the cleaning rod via the pivot section. The flexible insert rod of the cleaning brush is inserted through a through hole of the control device, when the control device is pivoted upwardly and locked in position when the control device is rotated downwardly.

2 Claims, 5 Drawing Sheets

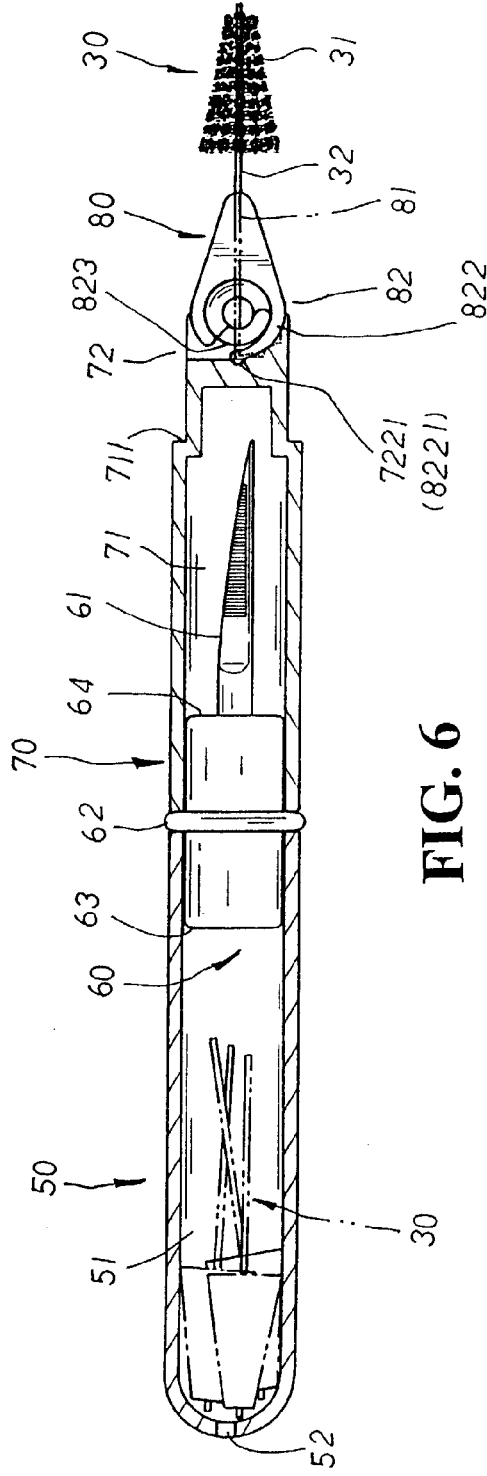
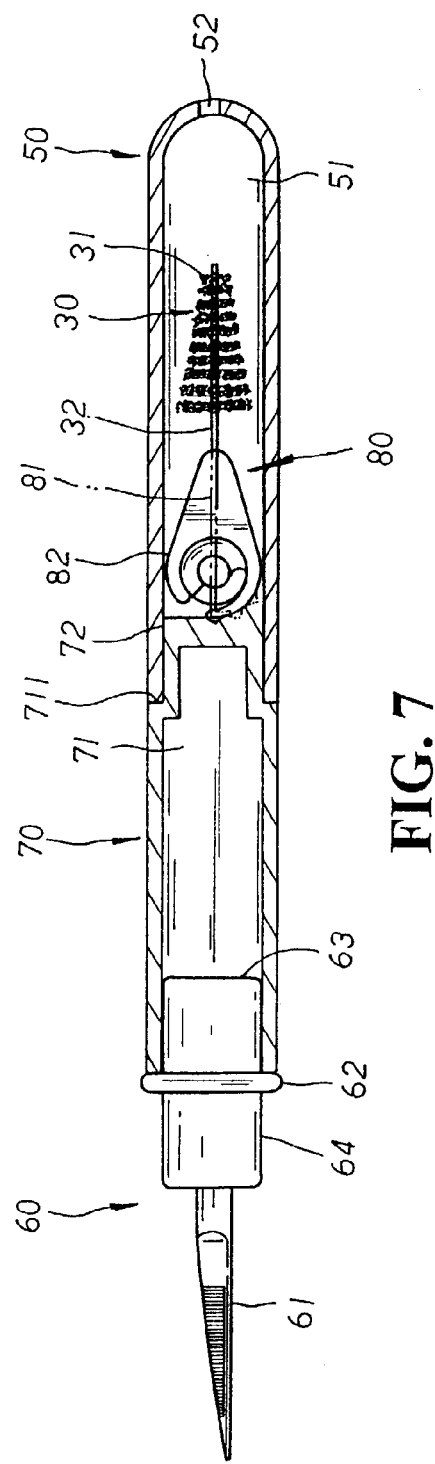
FIG. 6
FIG. 7

US 7,156,107 B2

TEETH CLEANING BRUSH STRUCTURE

BACKGROUND OF THE INVENTION

The present invention is related to a teeth cleaning brush structure, comprising a cleaning brush, a cover, a stick sleeve, a cleaning rod, and a control means wherein the cleaning brush has bristles disposed at one end and a flexible insert rod extending at the other end thereof to be adapted to a transverse through hole of the control means. The cover has an open receiving groove disposed at one end thereof for the stick sleeve with a cleaning stick disposed at one end to be adapted thereto. The cleaning rod is equipped with a hollow retaining chamber disposed at one end thereof, and a coupling section extending at the other end thereof for the control means to be pivotally joined thereto via a pivot section; whereby, the cleaning brush is assembled or replaced in an easy and fast manner without any other tools required. Besides, the cleaning brush can also be pivotally rotated to adjust the angle of the bristles suitably to the teeth in cleaning, achieving more efficient cleaning effect of the cleaning brush thereof.

Please refer to FIG. 1. Conventional tools for cleaning teeth include toothbrushes, or disposable dental floss, or toothpicks 10. Where the toothbrushes can't do to clear little pieces of food remained at the dental chinks, dental floss or toothpicks 10 are required as auxiliary tools to further clean the teeth. When going outside, one can only use dental floss or toothpicks 10 to simply clean the teeth; which, however, can't efficiently clear the remains of food or tartar on teeth. Thus, neither a simple nor a combined use of the conventional teeth cleaning tools can completely meet the need of users in cleaning teeth.

Please refer to FIG. 2. Another conventional teeth cleaning brush is mainly made up of a cleaning brush 20 having a handle 21 disposed at one end, and bristles 22 winding at the other end thereof. With the bristles 22 fixedly attached to the cleaning brush 20 thereof, the cleaning brush 20 must be discarded altogether once the bristles 22 are worn out of use, which is not only uneconomical but also increase the burden of the environment.

SUMMARY OF THE PRESENT INVENTION

It is, therefore, the primary purpose of the present invention to provide a teeth cleaning brush structure, comprising a cleaning brush, a cover, a stick sleeve, a cleaning rod, and a control means wherein the cleaning rod has a coupling section extending at one end thereof for the control means to be pivotally joined thereto via a pivot section; whereby, the control means is bent upwards in a straight angle to reveal a transverse through hole for the cleaning brush to be adapted thereto, and then rotated downwards to locate the cleaning brush in clamping abutment therein for use, providing a portable cleaning brush which is assembled or replaced in an easy and fast manner without any other tools required.

It is, therefore, the secondary purpose of the present invention to provide a teeth cleaning brush structure wherein, via the control means pivotally joined to the cleaning rod thereof, the cleaning brush can be pivotally rotated to adjust the angle of the bristles so as to suitably apply the bristles to the teeth in cleaning, achieving more efficient cleaning effect of the cleaning brush thereof

BRIEF DESCRIPTION OF THE DRAWINGS

FIG. 6 is a sectional view of the present invention in assembly.
FIG. 7 is a sectional view showing a cleaning stick of the present invention in use.

DETAILED DESCRIPTION OF THE PREFERRED EMBODIMENTS

Figure 1:
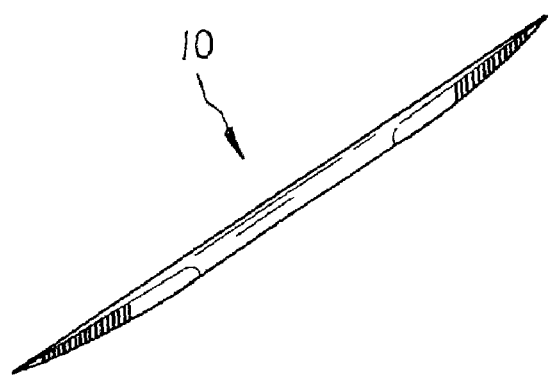
FIG. 1 is a perspective view of a conventional toothpick.
Figure 2:
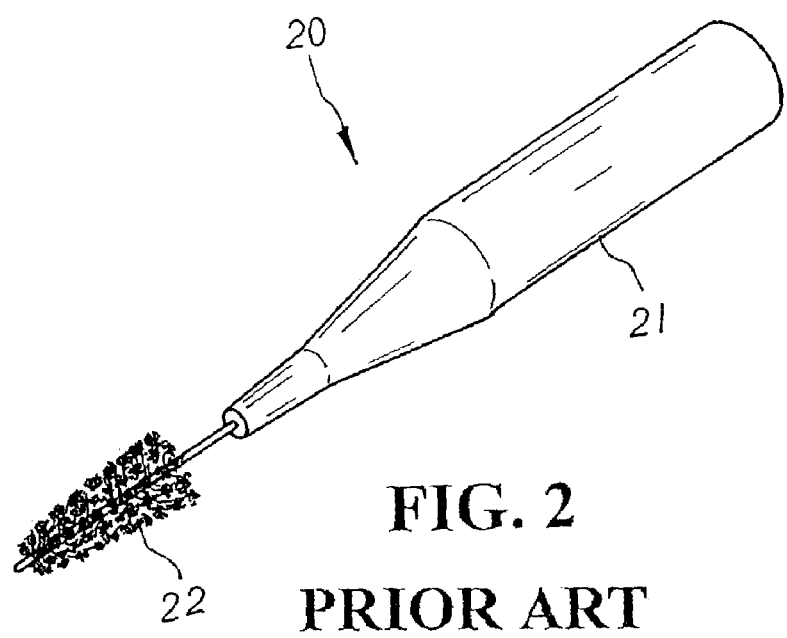
FIG. 2 is a perspective view of a conventional teeth cleaning brush.
Figure 3:
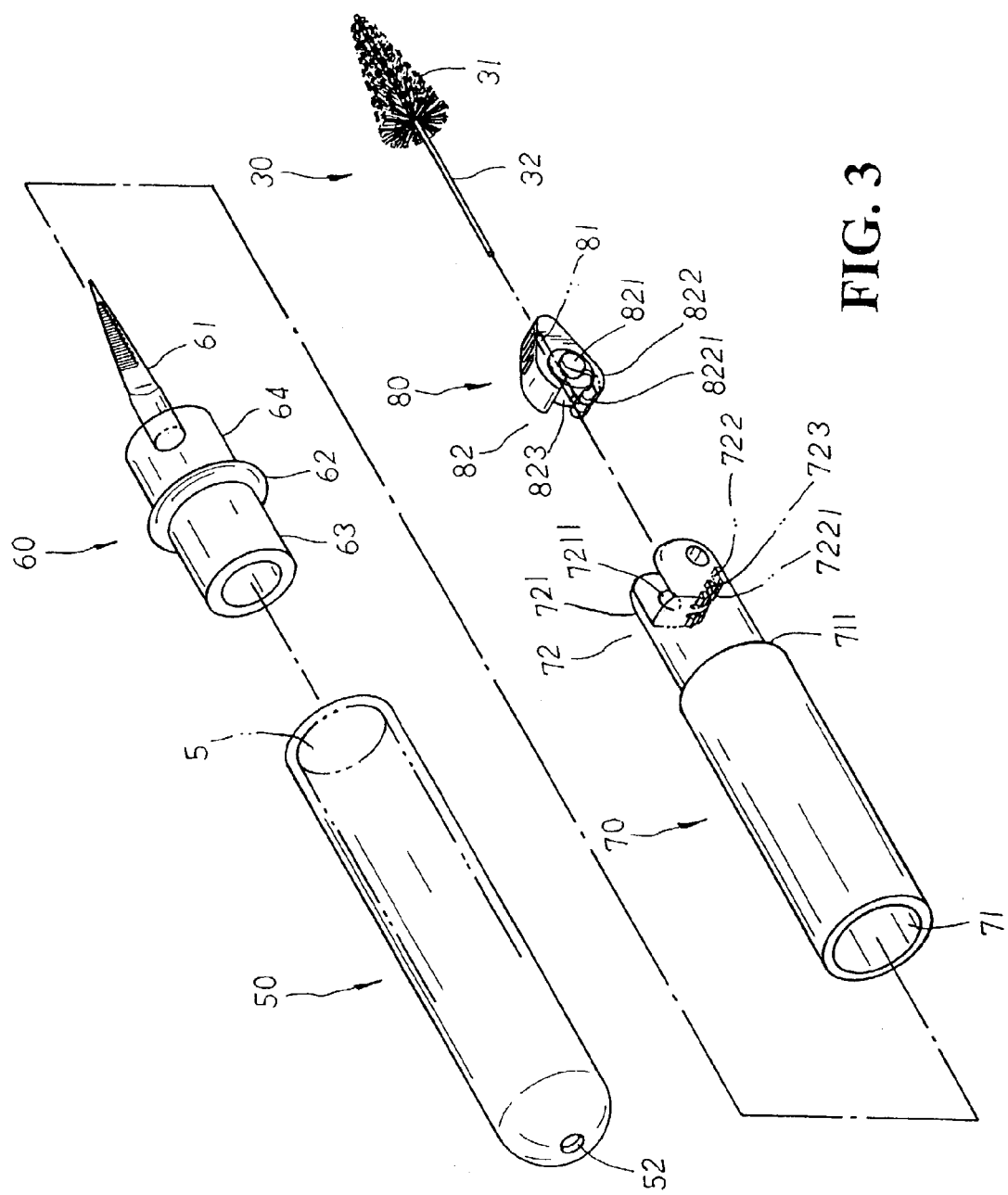
FIG. 3 is a perspective exploded view of the present invention.

Please refer to FIG. 3. The present invention is related to a teeth cleaning brush structure, comprising a cleaning brush 30, a cover 50, a stick sleeve 60, a cleaning rod 70, and a control means 80. The cleaning brush 30 is made up of bristles 31 winding in tapered circles at one end thereof, and a flexible insert rod 32 extending for a certain length at the bottom of the bristles 31 thereof. The cover 50 has an open receiving groove 51 disposed at one end thereof, and an air hole 52 disposed at the other closed end thereof. The stick sleeve 60 is provided with a cleaning stick 61 disposed at one end thereof, a stop ring 62 projecting at the middle of the other end thereof, and a left and a right sleeve parts 63, 64 disposed at both sides of the stop ring 62 thereof. The cleaning rod 70 has a hollow retaining chamber 71 disposed at one end thereof, a stop step flange 711 defining the other end thereof, and a coupling section 72 extending at one side of the stop step flange 711 thereof. A pair of symmetrical locating plates 721 each having a pivot hole 7211 disposed thereon are axially extended at the outer side of the coupling section 72 thereof. A pair of symmetrical arc guide facets 722 each having a plurality of insert grooves 7221 defined thereon is disposed at the lower inner side of the symmetrical locating plates 721, and an arc stop plate 723 is projecting at the middle of the symmetrical arc guide facets 722 thereof. The control means 80 has a transverse through hole 81 axially disposed at the center thereof, and a pivot section 82 disposed at one side thereof. The pivot section 82 thereof is equipped with two pivot posts 821 projecting at both lateral sides thereof, two symmetrical arc guide plates 822 each having an arc insert block 8221 disposed at one end thereof, and an arc stop face 823 disposed at the one side thereof.

Figure 4:
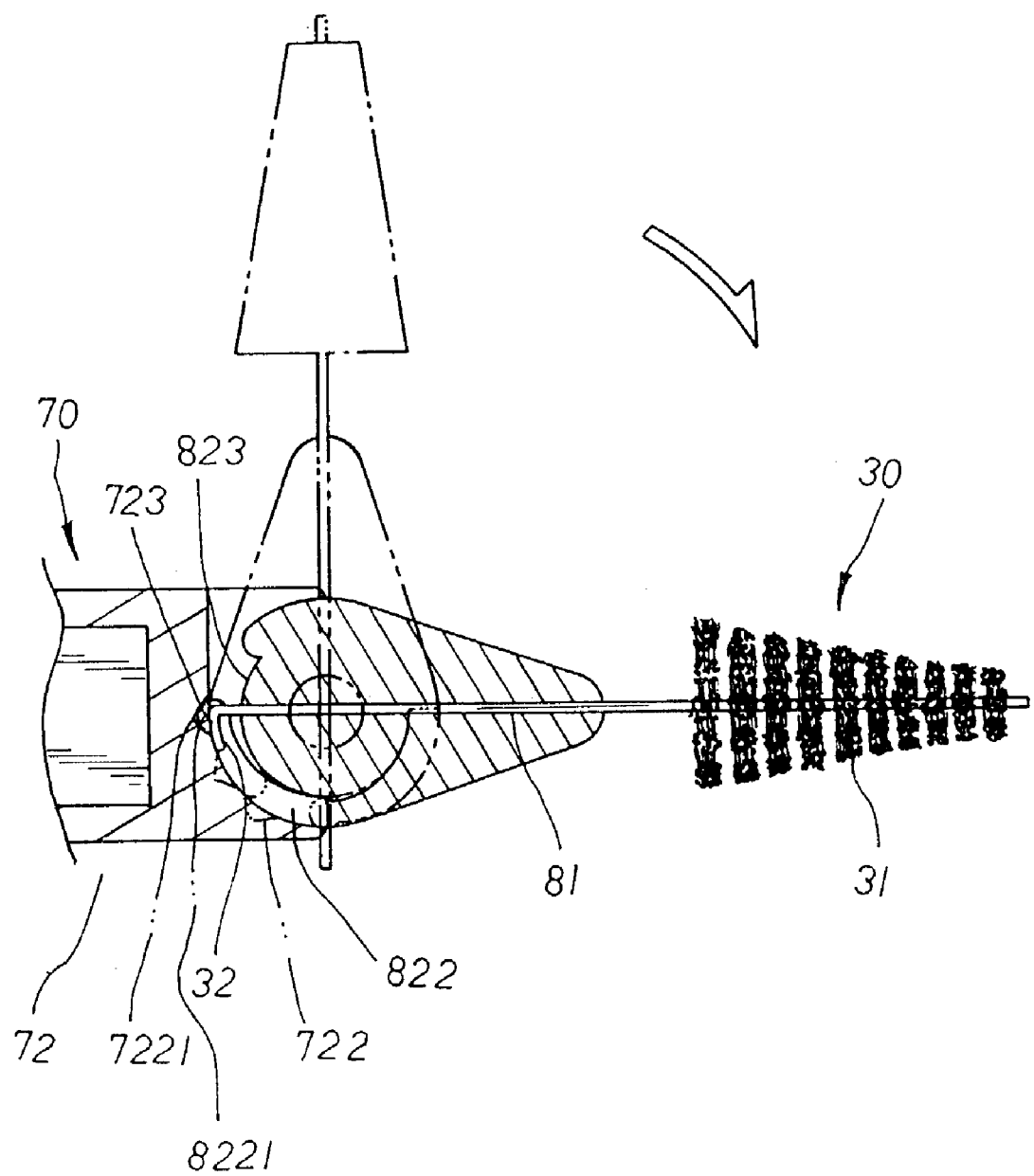
FIG. 4 is a partially cross sectional view of the present invention in operation.
Figure 5:
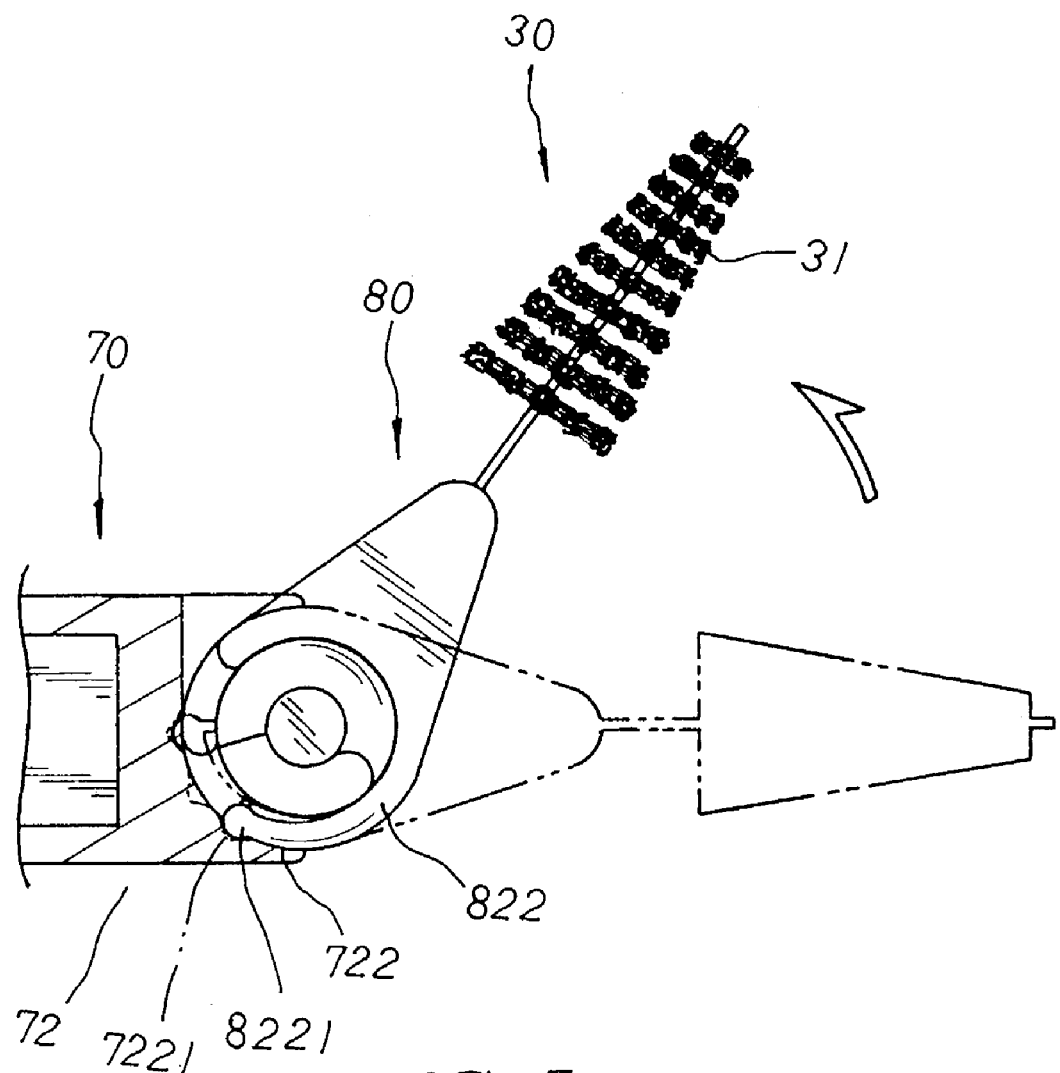
FIG. 5 is another cross sectional view showing the operation of a control means and cleaning brush of the present invention.

Please refer to FIG. 4. In assembly, the pivot section 82 of the control means 80 is pivotally mounted to the coupling section 72 of the cleaning rod 70 thereof. The pivot posts 821 thereof is pivotally joined to the pivot holes 7211 of the symmetrical locating plates 721, and the symmetrical arc guide plates 822 and arc stop face 823 thereof are respectively abutted against the symmetrical guide facets 722 and the arc stop plate 723 thereof. Thus, the control means 80 can be pivotally rotated up or down between the symmetrical locating plates 721 of the coupling section 72 therein with the arc insert block 8221 thereof engaged with the insert grooves 7221 thereof consecutively for location thereof. To replace or locate the cleaning brush 30 thereof, the control means 80 is bent upwards in a straight angle to reveal the transverse through hole 81 thereof vertically outside the symmetrical locating plates 721 thereof. The flexible insert rod 32 of the cleaning brush 30 is then led through the transverse through hole 81 till the bottom end thereof exposed outside the transverse through hole 81 thereof. The control means 80 is rotated downwards to bend the bottom end of the flexible insert rod 32 therewith in clamping abutment against the arc stop plate 723 and the arc stop face 823 thereof for location thereof. Thus, the cleaning brush 30 is pivotally moved with the rotation of the pivot section 82 of the control means 80 as so as to suitably adjust the angle of the bristle 31 thereof according to the location of teeth for cleaning, achieving more efficient cleaning effect as shown in FIG. 5.

Please refer to FIG. 6. The cleaning stick 61 of the stick sleeve 60 is adapted at the hollow retaining chamber 71 of the cleaning rod 70 therein and the stick sleeve 60 located onto the cleaning rod 70 via the right sleeve part 64 securely joined to the hollow retaining chamber 71 thereof with the stop ring 62 thereof abutted thereto. The cover 50 with a plurality of cleaning brushes 30 adapted at the receiving groove 51 therein is applied to the left sleeve part 63 of the stick sleeve 60 and engaged therewith to complete the assembly thereof.

Please refer to FIG. 7. To use the cleaning stick 61, the cover 50 is removed from the stick sleeve 60 and applied to the cleaning rod 70 thereof with the receiving groove 51 thereof joined to the coupling section 72 of the cleaning rod 70 till abutting against the stop step flange 711 thereof for location. The stick sleeve 60 is first removed from the cleaning rod 70 and then relocated in reverse thereto with the left sleeve part 63 thereof joined to the hollow retaining chamber 71 to reveal the cleaning stick 61 outside the cleaning rod 70 for use.

What is claimed is:

1. A teeth cleaning brush structure, comprising a cleaning brush, a cover, a stick sleeve, a cleaning rod, and a control device wherein the cleaning brush is made up of bristles winding in tapered circles at one end thereof, and a flexible insert rod extending for a certain length at the bottom of the bristles thereof;

the cover having an open receiving groove disposed at one end thereof, and an air hole disposed at a closed end thereof;

the stick sleeve having a cleaning stick disposed at one end thereof, a stop ring projecting at the middle of the other end thereof, and a left and a right sleeve parts disposed at both sides of the stop ring;

the cleaning rod having a hollow retaining chamber disposed at one end thereof, a stop step flange defining the other end thereof, and a coupling section extending at one side of the stop step flange;

the control device having a through hole axially disposed at a center thereof, the cleaning brush is inserted into the through hole, and a pivot section disposed at one side thereof matching to the coupling section of the cleaning rod;

the assembly, the control device is pivotally mounted to the coupling section of the cleaning rod via the pivot section thereof so that the control device rotates upwardly and downwardly between a pair of symmetrical locating plates of the coupling section;

whereby, when the control device is rotated upwardly, a bottom of the through hole is rotated downwardly away from the symmetrical locating plates and the flexible insert rod of the cleaning brush is inserted through the through hole; and when the control device is rotated downwardly, a bottom end of the flexible insert rod is protruding from the bottom of the through hole is bent securing the cleaning brush in the control device, the cleaning brush is pivotally rotated via the pivot section of the control device, wherein each of the pair of symmetrical locating plates has a pivot hole disposed thereon extending axially at the outer side thereof, a pair of symmetrical arc guide facets with a plurality of insert grooves defined thereon disposed at the lower inner side of the symmetrical locating plates thereof, and an arc stop plate projecting at the middle of the symmetrical arc guide facets thereof.

2. The teeth cleaning brush structure as claimed in claim 1, wherein the pivot section of the control device includes two pivot posts projecting at both lateral sides thereof, two symmetrical arc guide plates each having an arc insert block disposed at one end thereof, and an arc stop face disposed at the one side thereof.

\* \* \* \* \*